United States Patent [19]

Fex et al.

[11] 4,081,461

[45] Mar. 28, 1978

[54] ACYLATION PROCESS FOR THE PREPARATION OF PHENOLIC N-DISUBSTITUTED CARBAMATE ESTERS, AND ION PAIR SOLUTION FOR USE IN THE PROCESS

[75] Inventors: Hans Jacob Fex; Sten Krister Kristensson; Anders Robert Stamvik, all of Helsingborg, Sweden

[73] Assignee: Aktiebolaget Leo, Helsingborg, Sweden

[21] Appl. No.: 699,214

[22] Filed: Jun. 24, 1976

[30] Foreign Application Priority Data

Jul. 7, 1975 United Kingdom .............. 28604/75
Mar. 17, 1976 United Kingdom .............. 10824/76

[51] Int. Cl.² .......................................... C07C 125/06
[52] U.S. Cl. ................................ 260/397.4; 252/364;
260/268 C; 260/293.74; 260/295 CA;
260/295.5 C; 260/397.2; 260/397.5; 544/172;
560/115; 560/27; 560/32; 560/29; 560/31;
560/133; 560/134; 560/136; 560/137; 560/132;
560/21; 560/22
[58] Field of Search .................... 260/479 C, 247.2 B,
260/293.74, 268 C, 295.5 C, 295 CA

[56] References Cited

U.S. PATENT DOCUMENTS 4,082,779  4/1978  Fex et al. .................... 260/397.4

FOREIGN PATENT DOCUMENTS 1,016,959  1/1966  United Kingdom .............. 260/397.5

OTHER PUBLICATIONS

Gokel, Crown Ether Chemistry: Principles and Applications pp. 3–12. Aldrichimica Acta. 9 (1976).
Jones, Applications of Phase Transfer Catalysts in Organic Syn., p. 35, Aldrinchimia Acta. vol. 9, No. 3, 1976.

Primary Examiner—Natalie Trousof
Assistant Examiner—Jane T. Fan
Attorney, Agent, or Firm—Gordon W. Hueschen

[57] ABSTRACT

This invention relates to a novel carbamoylation method for the preparation of phenolic N-disubstituted carbamate esters, and novel compounds in said method. Phenolic carbamate esters are useful for various purposes, for instance as pharmaceuticals, e.g. antitumor agents, as biocides, e.g. pesticides, and intermediates for preparing such useful compounds.

32 Claims, No Drawings

ACYLATION PROCESS FOR THE PREPARATION OF PHENOLIC N-DISUBSTITUTED CARBAMATE ESTERS, AND ION PAIR SOLUTION FOR USE IN THE PROCESS

This invention relates to a novel carbamoylation method for the preparation of phenolic N-disubstituted carbamate esters, and novel compounds in said method. Phenolic carbamate esters are useful for various purposes, for instance as pharmaceuticals, e.g. antitumor agents, as biocides, e.g. pesticides, and intermediates for preparing such useful compounds.

BACKGROUND OF THE INVENTION

Phenolic carbamate esters are useful for various purposes, for instance as pharmaceuticals, e.g. antitumor agents, as biocides e.g. pesticides, and as intermediates for preparing such useful compounds. For example, phenolic N-bis(2-chloroethyl) carbamates, especially those deriving from phenols with estrogenic activity, are useful as antitumor agents or as intermediates for preparing such useful compounds (see e.g. Brit. Pat. No. 1.016.959 and Zimel, Neoplasma 12(1965):3, 297).

The best methods known and used for the preparation of phenolic N-disubstituted carbamates are the following:

(1) Reaction of a N-disubstituted carbamoyl chloride with a phenol.
(2) Reaction of a phenol chloroformate with a secondary amine.

These reactions are normally performed in pyridine or in an inert organic solvent in the presence of a suitable amine as a hydrogen chloride acceptor.

The existing methods are unsatisfactory for several reasons. Firstly, the use of pyridine or other amines in the reaction necessitates recovery steps in the process and/or gives environmental and pollution problems. Secondly, method 1 is not generally applicable and fails for some carbamoyl chlorides. Thirdly, method 2 is not directly applicable in many cases without recourse to protective groups when the phenol contains groups which might react in the preparation of the chloroformate (for instance alcoholic hydroxy groups).

It is an object of this invention, therefore, to provide an improved carbamoylation process for the preparation of phenolic N-disubstituted carbamates. It is also an object of this invention to provide an improved carbamoylation process for the manufacture of phenolic N-disubstituted carbamates, suitable for industrial practices and from which satisfactory yields and purity of the desired product can be obtained. Another object of the invention is to provide novel compounds and novel solutions, suitable as intermediates in said process. Further objects of the invention will become apparent hereinafter and still others will be apparent to one skilled in the art to which this invention pertains.

A known method for the catalysis of certain organic reactions is the so called "phase transfer catalysis" or "ion pair extraction". For reviews on this method see for instance J. Dockx — Synthesis 1973:8, 441 and E. V. Dehmlow — Angew. Chem. 86(1974):5, 187.

In such method the reaction of an organic compound (optionally dissolved in an organic solvent) with an ionized organic or inorganic compound is catalyzed by the presence of a phase transfer catalyst, i.e. a quaternary ammonium compound, or a Crown-ether (a macrocyclic polyether with metal complexing properties).

The function of the catalyst is to make the ionized compound, which normally is insoluble in organic solvents, soluble as an ion pair with the quaternary ammonium ion (or the Crown-ether complex with an alkali metal cation) in the organic phase, thus promoting the desired reaction with the organic compound. Normally, the reaction is performed in a two-phase solvent system consisting of water and a halogenated hydrocarbon solvent.

The method as known is mainly used for the alkylation of inorganic anions or anions from acidic organic compounds. The method is neither known nor supposed to work for acylation, including carbamoylation, of organic compounds, in as much as water or aqueous alkali is of necessity present in the method. Hydrolysis is therefore an expected side reaction in the method and acylating agents are sensitive to hydrolysis. Acyl chlorides are in fact notorious for their hygroscopicity and instability even under normal conditions of humidity, so that they are always stored only in tightly sealed containers.

Despite such contrary indications it has now been found that it is possible to perform carbamoylation of phenols using N-disubstituted carbamoyl chlorides, i.e. tertiary carbamoyl chlorides, in a phase transfer catalyzed reaction in the presence of aqueous alkali metal hydroxide and a phase transfer catalyst to form N-disubstituted phenolic carbamate esters. It has also been found that, by using at least one equivalent of catalyst (based on the phenolic compound), it is also possible to perform this reaction in two steps, the first step being a reaction of the phenolic compound, aqueous alkali metal hydroxide, phase transfer catalyst and water-immiscible solvent, followed by separation of the obtained organic phase containing the ion pair, and the second step being a reaction of the ion pair with an N-disubstituted carbamoyl chloride in the organic phase to form the desired ester. The organic phase containing the ion pair may be used as such in the second step, or the ion pair may be isolated and thereafter used in the second step. When the ion pair is isolated, other solvents may be used in the second step than those employed in the first step, if so desired.

The single-step procedure is generally preferred, but the two-step procedure is frequently advantageous in cases where the particular acyl chloride employed in characterized by the highest order of instability. Although in the case of the two-step process the organic solvent containing the ion-pair (which is contacted with the acyl chloride) is separated from the aqueous phase, the solution is completely saturated with water.

Procedure of the present invention remarkably and unpredictably proceeds directly to the desired carbamate esters in high yields and purity, without substantial hydrolysis or other deterioration of the unstable acid chlorides.

SUMMARY OF THE INVENTION

In one aspect, the invention provides for a process for the carbamoylation of the said phenolic hydroxy groups to form the said carbamate esters, comprising reacting in liquid phase the said phenolic compound, a tertiary carbamoyl chloride, an aqueous alkali metal hydroxide, and a phase transfer catalyst which is selected from the group consisting of a Crown-ether and a compound having the formula $Q^+X^-$; wherein $Q^+$ is selected from the group consisting of a quaternary ammonium cation and a quaternary phosphonium cation; and wherein $X^-$ is an inorganic anion.

Differently expressed, such process covers the preparation of compounds of the general formula:

$$AR_n \qquad (I)$$

by reaction of a suitably substituted phenolic compound $A(OH)_n$, an N-disubstituted carbamoyl chloride, aqueous alkali metal hydroxide, and a phase transfer catalyst $Q^+X^+$, according to the following reaction path:

$$A(OH)_n \rightarrow A(O^-Q^+)_n \rightarrow AR_n$$

In another aspect, the invention provides for an organic solvent solution containing an ion pair consisting of a quaternary ammonium or phosphonium cation or an alkali metal cation-Crown-ether complex and an anion of a phenol having a maximum of forty carbon atoms, and a tertiary carbamoyl chloride; an organic solvent solution containing an ion pair consisting of a quaternary ammonium or phosphonium cation or an alkali metal cation - Crown-ether complex and the anion of a phenolic estra-1,3,5(10)-triene, diphenyl substituted ethane, or diphenyl substituted ethene; such solution optionally containing also a tertiary carbamoyl chloride; and a novel intermediates, namely: tetralower-alkyl ammonium estra-1,3,5(10)-trien-17β-ol-3-olates and 17α-ethynyl derivatives thereof.

Expressed in a corresponding manner as per the general formula (I) above the ion pairs, either isolated as such or in solution, have the general formula:

$$A\text{-}(O^-Q^+)_n \qquad (II)$$

Further objects of the invention will become apparent hereinafter and still others will be apparent to one skilled in the art to which this invention pertains.

With regard to formulas (I) and (II) above, preferred embodiment are as follows. In formula (I) above, R is a tertiary carbamate ester group of the formula:

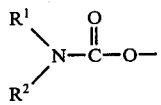

which is attached to a carbon atom of an aromatic ring system of A (as hereinafter defined), and wherein $R^1$ and $R^2$ are the same or different and are selected from the group consisting of alkyl, preferably containing at most six carbon atoms; alkenyl, preferably containing at most six carbon atoms; cycloalkyl, preferably containing at most six carbon atoms; phenylalkyl, preferably containing at most nine carbon atoms; and phenyl; and wherein $R^1R^2N$ may further be a ring system, preferably containing at most six atoms, which beside carbon atoms may include one or more further heteroatoms selected from the group consisting of O, S, and N; all of which under these definitions of $R^1$, $R^2$, and $R^1R^2N$ may be substituted with one or more of lower alkyl, lower alkenyl, lower alkoxy, —O—CO—$R^3$, halogen, —$CF_3$, —CN, —$NO_2$, —$COOR^4$, oxo, —$CONR^5R^6$, —$NR^7R^8$, and —$NR^9COR^{10}$ groups.

In formulas (I) and (II) above, $n$ is an integer selected from the group consisting of one and two.

In formulas (I) and (II) above, A is the radical of a compound containing a mono- or polycyclic ring system or ring systems, preferably having a maximum of 40 carbon atoms, inclusive of substituents always containing at least one aromatic ring (which may be a heteroaromatic ring) to which the group R (as above-defined), of formula (I) above, is attached; said radical A, excluding substituents, may contain at most four heteroatoms, selected from the group consisting of N, S, and O; the nonaromatic part of said radical A may contain one or more double or triple bonds; the said substituents of A being selected from lower alkyl, lower alkenyl, lower alkynyl, lower alkoxy, hydroxy, —O—CO—$R^{11}$, halogen, —$CF_3$, —CN, —$NO_2$, —$COOR^{12}$, oxo, —$CONR^{13}R^{14}$, —$NR^{15}R^{16}$, —$NR^{17}COR^{18}$, and R; wherein, in the above definitions of R and A, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are lower alkyl; $R^{11}$ may also be phenyl.

*Phase transfer catalyst* — The cation $Q^+$ of $Q^{30} X^-$ is selected from a quaternary ammonium cation preferably having a maximum of 40 carbon atoms, the substituents preferably being hydrocarbon radicals, and an alkali metal cation - Crown ether complex ("Crown ether" is the standard accepted nomenclature for a macrocyclic polyether containing ether groups separated by one to three carbon atoms, inclusive, and sometimes some of the oxygen atoms of the ether linkages are replaced by NH or S linkages, further information on this type of compounds can for instance be found in B. Dietrich — Chemie in unserer Zeit 7(1973):4, 120 and D. Bernabei — Kontakte 1973:2, 27), the Crown ether complex also preferably having a maximum of 40 carbon atoms. The Crown ether complex are prepared in a conventional manner as described in the above references and as further illustrated in the examples below.

Examples of suitable quaternary ammonium cations are tetraalkyl ammonium, alkyl trialkyl ammonium, aralkyl trialkyl ammonium such as tetrabutyl ammonium, tetrahexyl ammonium, tetrapropyl ammonium, benzyl triethyl ammonium, tetraethyl ammonium, benzyl trimethyl ammonium, cetyl trimethyl ammonium, dodecylbenzyl triethyl ammonium.

Examples of suitable Crown ether complexes are:

$K^+$-18-Crown-6 (1,4,7,10,13,16-hexaoxacyclooctadecane, $K^+$-dibenzo-18-crown-6 (2,3,11,12-dibenzo-1,4,7,10,13,16-hexaoxacyclooctadeca-2,11-diene),
$K^+$-dicyclohexyl-18-crown-6,
$K^+$-dibenzo-24-crown-8 (2,3,14,15-dibenzo-1,4,7,10,13,16,19,22-octaoxacyclotetracosa-2,14-diene),
$Na^+$-15-crown-5 (1,4,7,10,13-pentaoxacyclopentadecane),
$Na^+$-dibenzo-15-crown-5 (2,3,8,9-dibenzo-1,4,7,10,13-pentaoxacyclopentadeca-2,8-diene),
$Na^+$-cyclohexyl-15-crown-5,
$Na^+$-benzo-15-crown-5 (2,3-benzo-1,4,7,10,13-pentaoxacyclopentadecene-2), Examples of suitable Crown ether complexes, which are now frequently referred to as "Cryptates", are:

$K^+$-Kryptofix$^R$ 222 (4,7,13,16,21,24-hexaoxo-1,10-diazabicyclo/8.8.8./-hexacosane),
$Na^+$-Kryptofix$^R$ 221 (4,7,13,16,21-pentaoxa-1,10-diazabicyclo/8.8.5/-tricosane),
$Li^+$-Kryptofix$^R$ 211 (4,7,13,18-tetraoxa-1,10-diazabicyclo/8.5.5/-tricosane).

Such "Cryptates" are shown in the above-identified Bernabei publication in Kontakte.

As cation $Q^+$ of $Q^+X^-$ may also be employed tetrasubstituted quaternary phosphonium cations, the substituents preferably being hydrocarbon radicals. Suitable as such are, for instance, tetraalkyl phosphonium, alkyl trialkyl phosphonium, aralkyl trialkyl phosphonium, such as tetrabutyl phosphonium, benzyl triphenyl phosphonium and hexadecyl tributyl phosphonium cations.

No theoretical maximum number of carbon atoms for inclusion in the cation $Q^+$ exists, althogh, in general, a maximum of forty carbon atoms represents the upper limit imposed by certain practical limitations. Furthermore, a preferred upper limit regarding the number of carbon atoms of each individual alkyl or other substituent of the nitrogen or phosphorus atom of $Q^+$ is 20 carbon atoms.

The cation $Q^+$ of $Q^+X^-$ is preferably selected from tetrabutyl ammonium, benzyl trimethyl ammonium, benzyl triethyl ammonium, $K^+$-dibenzo-18-crown-6 and tetrabutyl phosphonium.

The anion $X^-$ of $Q^+X^-$ is an inorganic anion, preferably $Cl^-$, $Br^-$, $OH^-$, or $HSO_4^-$.

In this disclosure the term halogen refers to a halogen selected from fluorine, chlorine, and bromine.

In this disclosure the expression "lower" means that the group referred to contains one to four carbon atoms, inclusive. Thus, lower alkyl, lower alkenyl, lower alkynyl, and lower alkoxy include for instance: Methyl, ethyl, propyl, iso-propyl, butyl, secondary butyl, isobutyl, tertiary butyl, vinyl, iso-propenyl, 1-propenyl, allyl, ethynyl, 1-propynyl, 2-propynyl, methoxy, ethoxy, propoxy, iso-propoxy, butoxy, iso-butoxy, secondary butoxy, and tertiary butoxy.

*Reaction solvent* — According to the present invention, the reaction is conducted in a liquid phase. The liquid phase may be provided either by means of a suitable organic solvent for the reaction or by employing the acyl chloride as solvent. When an organic solvent is employed in the one-step procedure or in the first step of the two-step procedure, it may be any suitable organic solvent which is water-immiscible or has a limited miscibility with water and which is not reactive with the reactants or reaction products under the conditions of the reaction, so long as the ion pair, which constitutes a critical factor according to the invention, is soluble therein. This is because good extraction of the ion pair is essential to the high yields and recoveries of the ultimate product. If the ion pair is not sufficiently soluble in the organic solvent, then obviously less will be available for contact with the carbamoyl chloride, with corresponding loss from an economic standpoint.

In the two-step procedure, the solution of the ion pair may be used as such in the second step, the solvent in the second step thus being the same as in the first step. The ion pair may also be isolated from the solution obtained in the first step, and the second step then be performed in a solvent different from that employed in the first step. In this case an even wider range of solvents may be employed than in the one-step procedure or the first step of the two-step procedure.

The organic solvent should preferably have a boiling point not in excess of 150° C, to facilitate ready separation from the reaction products at the end of the reaction.

Suitable solvents for the one-step procedure, and the first step or the two-step procedure are halogenated aliphatic and aromatic hydrocarbons, aromatic hydrocarbons, ethers, esters, ketones, and alcohols. It is preferred that the ethers, esters, ketones, and alcohols are aliphatic.

Among the aromatic hydrocarbons, ethers, esters and ketones may be mentioned as representative solvents the following: Benzene, toluene, o-, m-, p-xylene, di-isopropyl ether, di-ethyl ether, ethyl acetate, isopropyl acetate, methyl isobutyl ketone and the like.

Halogenated aliphatic hydrocarbons are preferred, and especially preferred are chlorinated aliphatic hydrocarbons. Among the chlorinated aliphatic hydrocarbons, may be mentioned as representative solvents, the chloroalkanes, especially methylene chloride, chloroform, 1,2-dichloroethane, 1,1,2,2-tetrachloroethane, the chloroalkenes, especially cis-1,2-dichloroethylene, and the like.

Suitable solvents for the second step of the two-step process includes those mentioned above for the one-step procedure and the first step of the two-step procedure, but also others may be used, since in this case water-immiscibility is not necessary. Among such solvents may be mentioned lower alkanols; ethers, such as tetrahydrofurane and dioxane; amides, such as dimethyl formamide, dimethyl acetamide and formamide; and sulfoxides, such as dimethyl sulfoxide.

*Catalyst* — The catalysts are defined elsewhere in this document. The amount of catalyst, however, may vary widely without interfering with either the success of the reaction or the attainment of optimum yields and conversions. Catalytic amounts, as conventional in the art for catalytic reactions, are generally employed. However, any amount which is economically feasible may be employed. In the case of the two-step process, hereinbefore mentioned, at least an equivalent amount of catalyst, based upon the phenolic compound, may be employed. In the one-step process, amounts of catalyst ranging from 1–10% of the equivalent weight, again based upon the phenolic compound, may be employed, with about 5% being found entirely suitable. Whatever the amount of the catalyst employed, it is feasible and even desirable that the same be recovered at the end of one reaction, as it is advantageous from an economic standpoint that the catalyst be reused in a subsequent reaction and this is not only been found possible but it has become normal procedure.

*Time* — The reaction period may vary widely and is not critical, except that for best yields and recoveries and greatest economy the reaction must be allowed sufficient time to go to completion. In the case of the one-step process, with an excess of catalyst, the reaction is substantially instantaneous. When employing substantially the smaller amounts of catalyst, the reaction time is accordingly increased. In the two-step process with at least an equivalent amount of catalyst (based upon the phenol), the reaction is slower than in the one-step process, and the reaction time is accordingly increased. The reason for the slower reaction rate in the two-step process is probably that at higher concentration of ion-pair in the organic phase, larger aggregates of ion-parts are formed with a corresponding reduction of reactivity. It is only necessary that the reactants be maintained in efficient contact for a sufficient time for the reaction to go to completion and this is conducted in the usual manner, e.g. by efficient stirring, as would be apparent to anyone skilled in the art.

*Temperature* — The reaction may be conducted conveniently at room temperature. The reaction is frequently exothermic and can be controlled by the application of cooling water or ice in a normal manner if desired. The temperature, if exothermic, can also be controlled by controlling the amount of catalyst employed, as already mentioned, or by varying the rate of addition of the carbamoyl chloride to the dissolved ion-pair. Obviously, the reaction temperature is not critical except that it should not be so high as to produce undesirable side-effects or charring of ingredients or the reaction product, or so low that the reaction proceeds so slowly as to be at an uneconomic rate. As already stated, room temperature is usually satisfactory.

*Pressure* — The pressure used above the reaction mixture during the reaction is not particularly critical. For most purposes atmospheric pressure is adequate. In some cases, however, superatmospheric pressure may be desired and are servicable. The pressure may also be reduced, if desired.

*Molar ratios* — The carbamoyl chloride and the starting phenol are generally employed in approximately equivalent amounts. It is customary to ensure completion of the reaction to employ a slight excess of the carbamoyl chloride. Amounts of reactants varying from these parameters may also be employed with no detrimental effect whatever upon the reaction except loss of economy and the usually attendant problems of incompletely reacted starting materials in case less than equivalent amounts of either one of the reactants is employed.

*Work-up procedures* — The organic phase containing the desired product obtained after the reaction is worked up according to normal procedures, as apparent to those skilled in the art, i.e. the organic phase is washed with aqueous sulphuric acid to recover the catalyst for subsequent use, and the solvent is removed by distillation, preferably at reduced pressure to keep at a minimum the exposure of the product to elevated temperatures, the distillation residue then being purified by distillation, preferably at reduced pressure, or by recrystallization from a suitable solvent.

Among compounds covered by the above general formulas (I) and (II) those are preferred, wherein $R^1$ and $R^2$ of R are the same or different and are alkyl, preferably containing at most six carbon atoms, which may be substituted with halogen; wherein the radical A is a radical of a compound containing a mono- or polycyclic ring system or ring systems, which may be a tetra-cyclic ring system containing one benzene ring or a system consisting of two benzene rings linked together with a bridge, which may contain carbon atoms and at most two heteroatoms selected from N, S, and O; wherein the substituents of the radical A are selected from lower alkyl, lower alkenyl, lower alkynyl, lower alkoxy, $—O—CO—R^{11}$, halogen, and oxo.

Especially preferred are compounds wherein A is the radical of a compound having estrogenic activity.

Compounds, wherein $R^1$ and $R^2$ are 2-chloroethyl, are particularly preferred.

Tetracyclic ring compounds, wherein A is the radical of an estra-1,3,5(10)-triene, are particularly preferred. Compounds of this type, from which the radical A is derived, may be exemplified as follows:

estra-1,3,5(10)-trien-3-ol-17-one(estrone)
estra-1,3,5(10)-trien-3,17β-diol(estradiol-17β)
estra-1,3,5(10)-trien-3,17α-diol(estradiol-17α)
estra-1,3,5(10)-trien-3,16α,17β-triol(estriol)
estra-1,3,5(10)-trien-3,16β,17β-triol(16-epiestriol)
estra-1,3,5(10)-trien-3,16α,17α-triol(17-epiestriol)
estra-1,3,5(10)-trien-3,16α-diol-17-one
estra-1,3,5(10)-trien-3,17β-diol-16-one(16-ketoestradiol)
17α-ethynylestra-1,3,5(10)-trien-3,17β-diol(17β-ethynylestradiol)

and ethers and esters of any of the foregoing, many of which are known.

In this disclosure the steroids are numbered in accordance with the I.U.P.A.C. 1957 Rules for Nomenclature of Steroids.

Among the compounds, wherein A is the radical of a compound containing two benzene rings linked together with a bridge, those where A is the radical of a diphenyl-substituted ethane or ethene are preferred. Compounds of this type, from which the radical A derives and which are particularly preferred are:

3,4-bis/4-hydroxyphenyl/-hexene-3 (diethylstilbestrol)
3,4-bis/4-hydroxyphenyl/-hexa-2,4-diene (dienestrol)
3,4-bis/4-hydroxyphenyl/-hexane (hexestrol).

The N-disubstituted carbamoyl halides used as starting materials are either commercially available or are prepared according to known methods by reaction of the corresponding secondary amine with phosgene (see for instance Ullmanns Encyklopaedie der technischen Chemie 5(1954), 72).

The innumerable starting compounds providing the radical A are known and readily available. In general any phenolic compound, i.e. a compound having an aromatic ring, including heteroaromatic ring, bearing a hydroxy group may be used.

The compounds named in the following examples and being within the scope of the general formula (I) above, are of particular interest for the intended purposes. The examples are intended to illustrate but not to limit the scope of the invention.

EXAMPLE 1

To a solution of 1150 g tetrabutylammonium hydrogen sulphate in 20 liter water is added 7.3 liter 5M sodium hydroxide solution and 9 kg estradiol-17β.

The mixture is stirred vigorously at room temperature for ten minutes whereupon a solution of 7.45 kg N,N-bis(2-chloroethyl) carbamoyl chloride in 80 liter chloroform is added. The vigorous stirring is continued for about two hours or until the estradiol is completely dissolved and the reaction mixture consists of two clear phases.

The inorganic phase is discarded and the chloroform phase is washed thoroughly with a mixture of 1000 ml 5M sulphuric acid and 15 liter water. The chloroform phase is then washed with 20 liter water, dried over sodium sulphate and evaporated to a thick oil. The oil is dissolved in 150 liter methanol and left overnight at a temperature of about 0° C. The crystallized substance is filtered off and washed with 3 × 10 liter cold methanol. The product is dried in vacuo at a temperature of about 45° C to constant weight.

The product is estradiol-17β-3-N-bis(2-chloroethyl) carbamate which sinters at about 65°–70° C, solidifies and melts at 124°–125° C and is pure in TLC. The obtained yield is 13.1 kg (90%).

EXAMPLE 2

13.5 kg estrone is suspended in 50 ml 2M aqueous sodium hydroxide and 1.75 g tetrabutyl ammonium hydrogen sulphate is added. The mixture is stirred vigorously for five minutes and a solution of 11 g N,N-bis(2-chloroethyl) carbamoyl chloride in 200 ml chloroform is added. The resulting mixture is stirred for 4 hours at room temperature.

The inorganic phase is discarded and the organic phase is washed with 150 ml 2M sulphuric acid and then with 300 ml water. The solution is dried over magnesium sulphate, evaporated to 100 ml and passed through a column packed with alumina (length 50 cm, diameter 50 mm). The column is eluted with chloroform and the eluate evaporated to dryness.

The product is estrone-3-N-bis(2-chloroethyl) carbamate, which after recrystallization from 1200 ml methanol has a melting point of 145°–146° C and is pure in TLC. The obtained yield is 19.5 g (89%).

In substantially the same manner the following compounds are obtained from the corresponding starting materials.

estradiol-17$\beta$-acetate-3-N-bis(2-chloroethyl) carbamate, mp. 101°–102° C.

estradiol-17$\beta$-propionate-3-N-bis(2-chloroethyl)carbamate, mp. 72°–74° C estradiol-17$\beta$-pivalate-3-N-bis(2-chloroethyl)carbamate, mp. 110°–111° C estradiol-3,17$\beta$-bis/N-bis(2-chloroethyl) carbamate/, mp. 92.5°–93.5° C from estradiol-17$\beta$-N-bis(2-chloroethyl) carbamate and N,N-bis(2-chloroethyl) carbamoyl chloride estradiol-17$\beta$-3-N-bis(2-chloropropyl) carbamate, mp. 114°–116° C estradiol-17$\beta$-3-N-bis(2-bromoethyl) carbamate, mp. 80° C estradiol-17$\beta$-3-N-(2-chloroethyl)-N-methyl carbamate, mp. 162°–164° C estradiol-17$\beta$-3-N-(2-chloroethyl)-N-(3-chloropropyl) carbamate. mp. 79°–87° C 17$\alpha$-ethynylestradiol-3-N-bis(2-chloroethyl) carbamate, mp. 140°–141° C estriol-16$\alpha$-acetate-3-N-bis(2-chloroethyl) carbamate, mp. 154°–156° C 16-ketoestradiol-3-N-bis(2-chloroethyl) carbamate, mp. 19°–200° C estradiol-17$\alpha$-3-N-bis(2-chloroethyl) carbamate, mp. 104.5°–106° C estriol-16$\alpha$,17$\beta$-diacetate-3-N-bis(2-chloroethyl) carbamate, mp. 107°–109° C diethylstilbestrol-O-methyl ether-O'-/N-bis(2-chloroethyl) carbamate/, mp. 96.5°–98° C diethylstilbestrol-O-benzoate-O'-/N-bis(2-chloroethyl) carbamate/, mp. 80°–82° C diethylstilbestrol-bis/N-bis(2-chloroethyl) carbamate/, mp. 140°–143° C dienestrol-bis/N-bis(2-chloroethyl) carbamate/, mp. 136°–137° C hexestrol-bis/N-bis(2-chloroethyl) carbamate/, mp. 148°–150° C 2,2-bis/4-N-bis(2-chloroethyl)carbamoyloxyphenyl/-propan, mp. 181°–182° C 5,6,7,8-tetrahydro-2-naphtyl-N-bis(2-chloroethyl) carbamate, mp. 77° C 17$\alpha$-ethylestradiol-3-N-bis(2-chloroethyl) carbamate, mp. 115°–117° C 2-naphthyl-N-bis(2-chloroethyl) carbamate, mp. 65°–67° C 1-naphthyl-N-bis(2-chloroethyl) carbamate, mp. 80°–82° C phenyl-N-bis(2-chloroethyl) carbamate, bp$_3$. 165°–170° C 2,6-dimethylphenyl-N-bis(2-chloroethyl) carbamate, mp. 95° C 4-chlorophenyl-N-bis(2-chloroethyl) carbamate, bp$_{0.01}$ 153° C 2-methoxycarbonylphenyl-N-bis(2-chloroethyl) carbamate, mp. 83° C 2,4,6-trichlorophenyl-N-bis(2-chloroethyl) carbamate, mp. 71°–72° C phloroglucinol-1,3-dibenzoate-5-N-bis(2-chloroethyl) carbamate, mp. 81°–3° C 4,4'-bis/N-bis(2-chloroethyl)carbamoyloxy/-trans-stilbene, mp. 136°–38° C 4,4'-bis/N-bis(2-chloroethyl)carbamoyloxy/benzil, mp. 118°–119° C 4,4'-bis/N-bis(2-chloroethyl)carbamoyloxy/benzophenone, mp. 94°–95° C 4,4'-bis/N-bis(2-chloroethyl)carbamoyloxy/diphenylmethane, mp. 47°–49° C 4,4'-bis/N-bis(2-chloroethyl)carbamoyloxy/bibenzyl, mp. 100°–102° C 4,4'-bis/N-bis(2-chloroethyl)carbamoyloxy/azobenzene, mp. 128°–129° C 4,4'-bis/N-bis(2-chloroethyl)carbamoyloxy/diphenyl ether, mp. 89°–90° C 4,4'-bis/N-bis(2-chloroethyl)carbamoyloxy/diphenyl sulfide, mp. 62°–64° C 4,4'-bis/N-bis(2-chloroethyl)carbamoyloxy/diphenyl sulfone, mp. 115°–117° C 4,4'-bis/N-bis(2-chloroethyl)carbamoyloxy/chalcone, mp. 88°–89° C 2,2-bis/4-N-bis(2-chloroethyl)carbamoyloxyphenyl/butane, mp. 119°–120° C 3,3-bis/4-N-bis(2-chloroethyl)carbamoyloxyphenyl/-pentane, mp. 96°–98° C 4,4'-bis/N-bis(2-chloroethyl)carbamoyloxy/diphenyl, mp. 152°–154° C

EXAMPLE 3

To illustrate the reuse of phase transfer catalyst, the aqueous sulphuric acid phase, obtained in the work up procedure of Example 2, is neutralized with a sufficient amount of aqueous 10 M sodium hydroxide. The obtained solution, containing the phase transfer catalyst, is added to a suspension of 13.5 g estrone in 50 ml aqueous 2 M sodium hydroxide. The resulting mixture is treated as in example 2, giving estrone-3-N-bis(2-chloroethyl) carbamate in a yield of 19.2 g (88%).

EXAMPLE 4

In substantially the same manner as in Example 2, but starting from estrone and using tetrabutylammonium bromide as phase transfer catalyst, estrone-3-N-bis(2-chloroethyl) carbamate is obtained in a yield of 18.5 g (84%).

EXAMPLE 5

In substantially the same manner as in Example 2, but using benzyl trimethyl ammonium chloride as phase transfer catalyst, estrone-3-bis(2-chloroethyl) carbamate is obtained in a yield of 19.1 g (85%).

EXAMPLE 6

6.81 g estradiol-17$\beta$ is suspended in a solution of 1.31 g potassium hydroxide in 15 ml water. 0.9 g dibenzo-18-crown-6 is added to the suspension and thereafter a solution of 5.62 g N,N-bis(2-chloroethyl)carbamoyl chloride in 100 ml chloroform is added. The mixture is stirred at room temperature for 4 hours, whereafter the chloroform phase is separated and washed with 1-M sulphuric acid and water. The chloroform is evaporated from the solution in vacuo and the residual oil is recrystallized from methanol giving estradiol-17β-3-N-bis(2-chloroethyl) carbamate, which sinters at about 65°–70° C, solidifies, and melts at 124°–125° C. The obtained yield is 10.3 g (93.5%).

EXAMPLE 7

In substantially the same manner as in example 6, but using Kryptofix®222 as phase transfer catalyst, estrone-3-N-bis-(2-chloroethyl) carbamate is obtained in a yield of 18.3 g (83%).

EXAMPLE 8

To a solution of 35 g tetrabutyl ammonium hydrogen sulphate in 100 ml aqueous 2 M sodium hydroxide is added 27.2 g estradiol-17β. The mixture is stirred for 15 minutes and then extracted with 2×100 ml chloroform. The chloroform phase is dried over magnesium sulphate and filtered. A solution of 13.5 g N,N-diethyl carbamoyl chloride in 100 ml chloroform is added and the solution boiled for 4 hours. The solution is then washed with 300 ml water, 300 ml 2 M sulphuric acid and finally with 300 ml water. The solution is then evaporated to dryness, dissolved in 200 ml chloroform and chromatographed on alumina. The column is eluted with chloroform and the eluate evaporated to dryness.

The product is estradiol-17β-3-N-diethyl carbamate, which after recrystallization from methanol has a melting point of 198°–200° C and is pure in TLC. The obtained yield is 9.3 g (55%).

In substantially the same manner the following compounds are obtained from the corresponding starting materials.

estradiol-17β-acetate-3-N-diethyl carbamate, mp. 148°–151° C,
estrone-3-N-diethyl carbamate, mp. 180° C,
5,6,7,8-tetrahydro-2-naphtyl N-diethyl carbamate, mp. 62°–63° C,
2-naphtyl N-di-n-amyl carbamate, $bp_5$ 220°–225° C,
m-dimethylaminophenyl N-dimethyl carbamate, $bp_{20}$ 194°–197° C,
m-dimethylaminophenyl N-benzyl-N-methyl carbamate, $bp_{20}$ 270°–275° C,
m-dimethylaminophenyl N-methyl-N-phenyl carbamate, mp. 82°–84° C,
3-tert butylphenyl N-cyclohexyl N-ethyl carbamate, mp. 56°–57° C,
3-tert butylphenyl 4-morpholinecarboxylate, mp. 85°–86° C,
3tert butylphenyl 1-piperidinecarboxylate, mp. 66°–67° C,
3-tert butylphenyl 1-(4-methylpiperazine)carboxylate, mp. 74°–76° C,
4-butoxycarbonylphenyl 1-piperidinecarboxylate, $bp_5$ 212°–214° C,
3-(N-tetramethylenecarbamoyloxy)pyridine, mp. 64°–66° C,
2,6-dimethyl-4-pyridyl N-dimethyl carbamate, mp. 73°–74° C,
3-ethoxyphenyl N-diethyl carbamate, $bp_5$ 150°—155° C,
3-tert butylphenyl N-bis(n-hexyl) carbamate, $bp_{0.1}$ 160°–162° C.

EXAMPLE 9

10.88 g estradiol-17β is suspended in 20 ml 5-M sodium hydroxide and 1.4 g dodecylbenzyl triethyl ammonium chloride is added. 8.97 g N,N-bis(2-chloroethyl) carbamoyl chloride is dissolved in 150 ml chloroform and added to the above mixture at room temperature. The mixture is stirred for 4 hours at this temperature. The chloroform phase is separated and washed successively with 1-M hydrochloric acid and water. The solution is evaporated in vacuo and the residue is recrystallized from methanol giving estradiol-17β-3-N-bis(2-chloroethyl) carbamate, which sinters at about 65°–70° C, solidifies, and melts at 124°–125° C. The obtained yield is 15.0 g (85%).

EXAMPLE 10

To illustrate the isolation of the ion pair, 5.44 g estradiol-17β is thoroughly mixed with 6.8 g tetrabutyl ammonium hydrogen sulphate and 44 ml 1-M sodium hydroxide solution is added. The mixture is stirred for 10 minutes after addition of 150 ml chloroform. Air is excluded by use of nitrogen gas. The chloroform phase is separated, evaporated in vacuo, and the residue treated with acetone, filtered and dried in vacuo. The product is tetrabutyl ammonium estra-1,3,5(10)-trien-17β-ol-3-olate. The produt has no defined melting point, but decomposes at about 190° C. The structure is confirmed by NMR, the NMR data obtaining being:

Chemical shift (peak structure, number of hydrogens): 0.65 – 2.4($m$, 44H) with 0.69 ($s$, 3H), 0.96 ($t$, 12H), 2.45–2.9 ($m$, 2H), b 2.95–3.4 ($m$, 8H), 3,60 ($t$, 1H), 6.45–6.65 ($m$, 2H), 7.02 ($d$, 1H), solvent DMSO/D$_2$O/CDCl$_3$.

In substantially the same manner tetrabutyl ammonium 17β-ethynyl-estra-1,3,5(10)-trien-17β-ol-3-olate is obtained from 17β-ethynyl-estradiol and tetrabutyl ammonium hydrogen sulphate. The structure is confirmed by NMR, and NMR data obtained being:

0.7 – 2.9 ($m$, 46H) with 0.78 ($s$, 3H), 0.92 ($t$, 12H), 2.9 – 3.5 ($m$, 9H), with 3.22 ($s$, 1H), 6,3 – 6.55 ($m$, 2H), 6.91 ($d$, 1H). Solvent: ;i d$_6$-DMSO.

The abbreviations for peak structure above in the NMR data: $s$ means singlet, $d$ means doublet, $t$ means triplet and $m$ means multiplet.

EXAMPLE 11

To illustrate the preparation of the ion pair in solution, 272 mg β-estradiol is thoroughly mixed with 340 mg tetrabutyl ammonium hydrogen sulphate, and 3 ml 2-M sodium hydroxide solution is added. To the mixture 5 ml deutero-chloroform (this solvent is used for the purpose of structure confirmation by NMR by direct use of the solution obtained) is added and the mixture is efficiently stirred for 10 minutes. Air is excluded by use of nitrogen gas. The chloroform phase is filtered through a plug of cotton to remove water, and the solution obtained is analyzed by NMR. The product obtained (in solution) is tetrabutyl ammonium estra-1,3,5(10)-trien-17β-ol-3-olate, the structure of which is confirmed as stated by NMR.

The NMR data obtained is:

Chemical shift (peak structure, member of hydrogens): 0.7 – 2.5 ($m$, 44H) with 0.76 ($s$, 3H), 0.95 ($t$, 12H), 2.70 ($m$, 2H), 3.0 – 3.4 ($m$, 8H), 3.75 ($t$, 1H), 6.55 – 6.75 ($m$, 2H), b 7.0 ($d$, 1H), solvent CDCl$_3$. The abbreviations used are explained in the preceding example.

In substantially the same manner the following ion pairs are obtained, the structure being confirmed by NMR as above:

tetrabutyl ammonium estra-1,3,5-(10)-trien-17-on-3-olate from estrone, the NMR data being 0.75 – 2.6 (m, 44H) with 0.88 (s, 3H), 0.94 (t, 12H); 2.74 (m, 2H), 2.9 – 3.4 (m, 8H), 6.5 – 6.7 (m, 2H) 6.97 (d, 2H), solvent $CDCl_3$ and tetrabutyl ammonium estra-1,3,5(10)-trien-17$\beta$-acetate-3-olate from estradiol-17$\beta$-acetate, the NMR data being 0.75 – 2.5 (m, 47H) with 0.82 (s, 3H), 0.93 (t, 12H), 2.03 (s, 3H); 2.66 (m, 2H), 3.0 – 3.45 (m, 8H), 4.65 (t, 1H), 6.45 – 6.7 (m, 2H), 6.93 (d, 1H), solvent $CDCl_3$.

Also obtained the structure-confirmed by NMR in substantially the same manner from estradiol-17$\beta$ and a corresponding phase transfer catalyst as given below are the following:

tetrahexyl ammonium estra-1,3,5(10)-trien-17$\beta$-ol-3-olate from tetrahexyl ammonium hydrogen sulphate,
tetrapropyl ammonium estra-1,3,5(10)-trien-17$\beta$-ol-3-olate from tetrapropyl ammonium hydrogen sulphate,
tetrabutyl phosphonium estra-1,3,5(10)-trien-17$\beta$-ol-3-olate from tetrabutyl phosphonium chloride.
cetyl trimethylammonium estra-1,3,5(10)-trien-17$\beta$-ol-3-olate from cetyl trimethyl ammonium bromide,
potassium dibenzo-18-crown-6 estra-1,3,5(10)-trien-17$\beta$-ol-3-olate from dibenzo-18-crown-6,
potassium dicyclohexyl-18-crown-6 estra-1,3,5(10)-trien-17$\beta$-ol-3-olate from dicyclohexyl-18-crown-6,
dodecylbenzyl triethyl ammonium estra-1,3,5(10)-trien-17$\beta$-ol-3-olate from dodecylbenzyl triethyl ammonium chloride,
potassium 18-crown-6 estra-1,3,5(10)-trien-17$\beta$-ol-3-olate from 18-crown-6.
potassium dibenzo-24-crown-8 estra-1,3,5(10)-trien-17$\beta$-ol-3-olate from dibenzo-24-crown-8,
sodium dibenzo-15-crown-5 estra-1,3,5(10)-trien-17$\beta$-ol-3-olate from dibenzo-15-crown 5,
sodium cyclohexyl-15-crown-5 estra-1,3,5(10)-trien-17$\beta$-ol-3-olate from cyclohexyl-15-crown-5,
lithium 4,7,13,18-tetraoxa-1,10-diazabicyclo-/8.5.5/-tricosane estra-1,3,5(10)-trien-17$\beta$-ol-3-olate from 4,7,13,18-tetraoxa-1,10-diazabicyclo-/8.5.5./-tricosane,
hexadecyl tributyl phosphonium estra-1,3,5(10)-trien-17$\beta$-ol-3-olate from hexadecyl tributyl phosphonium bromide.

EXAMPLE 12

5.44 g $\beta$-estradiol is suspended in 10 ml 5-M sodium hydroxide. 4.8 g tetrabutyl ammonium hydrogen sulphate is added. While stirring efficiently, a solution of 4.5 g of N,N-bis(2-chloroethyl) carbamoyl chloride dissolved in 100 ml ethyl acetate is added. The mixture is agitated for 4 hours at room temperature. The organic phase is separated and washed with water. The solution is evaporated in vacuo and the residue is recrystallized from methanol giving estradiol- 17$\beta$-3-N-bis(2-chloroethyl) carbamate, which sinters at about 65°–70° C, solidifies, and melts at 124°–125° C. The obtained yield is 84%.

In substantially the same manner, the same compound is obtained in similar yield and purities by using the following reaction solvents: Methyl isobutyl ketone, tetrachloroethylene, isoporpyl ether and isopropyl acetate.

EXAMPLE 13

To illustrate the superiority of the invention over existing known methods, 75 g estradiol-17$\beta$ is dissolved in 300 ml pyridine. The solution is cooled to 0° C and 120 g N,N-bis(2-chloroethyl) carbamoyl chloride is added. The resulting mixture is slowly heated to 35° C and kept at this temperature for 96 hours. 100 g ice is added and the obtained clear solution is slowly added to a mixture of 500 g ice and 1200 ml 5-M hydrochloric acid. The precipitated product is filtered, washed with water and recrystallized twice from methanol to give estradiol-3-N-bis-(2-chloroethyl) carbamate in a yield of 49%.

In substantially the same manner estradiol-3-N-diethyl carbamate is obtained from estradiol-17$\beta$ and N,N-diethyl carbamoyl chloride. The melting point is 192°–194° C and the obtained yield is 12%.

From the foregoing examples it is apparent that the preferred phenolic compounds providing the radical A are selected from the group consisting of 3-hydroxy aromatic A-ring steroids having pharmacological activity or a 3-hydroxy aromatic A-ring steroid, which is an intermediate for such active compounds, especially 3-hydroxy-1,3,5(10)-estratrienes; hydroxydiphenyl alkanes and alkenes; heterobridged hydroxydiphenyls; hydroxydiphenyls; hydroxynaphtalenes; hydroxybenzenes; and hydroxypyridines; and that the preferred carbamoyl chlorides are selected from the group consisting of bis($\omega$-halo-lower alkyl)carbamoyl chlorides, especially the $\omega$-chloro compounds and particularly N-bis(2-chloroethyl)carbamoyl chloride; and bis(lower alkyl) carbamoyl chlorides.

It is to be understood that the invention is not limited to the exact details of operation or exact compounds shown or described, as obvious modifications and equivalents will be apparent to one skilled in the art, and the invention is therefore to be limited only by the scope of the appended claims.

We claim:
1. In a process for the carbamoylation of phenolic hydroxy groups to form carbamate esters, comprising reacting in liquid phase a phenolic compound, and a tertiary carbamoyl chloride, the improvement which comprises using an aqueous alkali metal hydroxide and a phase transfer catalyst which is selected from the group consisting of a Crown-ether and a compound having the formula $Q^+X^-$; wherein $Q^+$ is selected from the group consisting of a quaternary ammonium cation and a quaternary phosphonium cation; and wherein $X^-$ is an inorganic anion.

2. In a process for the carbamoylation of phenolic hydroxy groups to form carbamate esters, comprising reacting in liquid phase a phenolic compound and a tertiary carbamoyl chloride, the improvement which comprises using an aqueous alkali metal hydroxide and a phase transfer catalyst which is selected from the group consisting of a Crown-ether and a compound having the formula $Q^+X^-$, wherein $Q^+$ is selected from the group consisting of a quaternary ammonium cation and a quaternary ammonium phosphonium cation, wherein $X^-$ is an inorganic anion, and wherein the reaction is performed in one step using a catalytic amount of the phase transfer catalyst.

3. In a process for the carbamoylation of phenolic hydroxy groups to form carbamate esters, comprising reacting in liquid phase a phenolic compound and a tertiary carbamoyl chloride, the improvement which comprises using an aqueous alkali metal hydroxide and a phase transfer catalyst which is selected from the group consisting of a Crown-ether and a compound having the formula $Q^+X^-$, wherein $Q^-$ is selected from the group consisting of a quaternary ammonium cation and a quaternary phosphonium cation, wherein $X^-$ is an inorganic anion, and wherein the reaction is performed in two steps, the first step comprising reaction of the phenolic compound, the aqueous alkali metal hydroxide, and phase transfer catalyst in at least an equivalent amount based upon the phenolic compound, in a water-immiscible non-reactive organic solvent which is not reactive with the reactants or reaction products under the conditions of reaction and in which the ion-pair is soluble, followed by separation of the obtained organic phase containing the resulting ion-pair dissolved therein, and the second step comprising reaction of the ion-pair with the carbamoyl chloride to form the desired carbamate ester.

4. Process of claim 2, wherein the phase transfer catalyst is used in an amount ranging from one to ten percent of the equivalent weight based upon the phenolic compound.

5. Process of claim 2, wherein the reaction is performed in a water-immiscible non-reactive organic solvent.

6. Process of claim 3, wherein the organic phase, containing the ion-pair obtained in the first step, is used directly in the second step without isolation.

7. Process of claim 3, wherein the organic solvent is a chlorinated aliphatic hydrocarbon.

8. Process of claim 5, wherein the organic solvent is a chlorinated aliphatic hydrocarbon.

9. Process of claim 1, wherein the reaction is conducted at about room temperature.

10. Process of claim 1, wherein the cation is a quaternary ammonium cation.

11. Process of claim 1, wherein the carbamoyl chloride is a bis(omega-halo-lower alkyl)carbamoyl chloride.

12. Process of claim 10, wherein the organic groups in the quaternary ammonium cation are selected from alkyl and benzyl.

13. Process of claim 10, wherein the cation is tetrabutyl ammonium or benzyl trimethyl ammonium.

14. Process of claim 1, wherein the inorganic anion is selected from the group consisting of $Cl^-$, $Br^-$, $HSO_4^-$, and $OH^-$.

15. In a process for the carbamoylation of steroid or diphenylethane or diphenylethene phenolic hydroxy groups to form corresponding carbamate esters, comprising reacting in liquid phase the said compound and a tertiary carbamoyl chloride, the improvement which comprises using an aqueous alkali metal hydroxide and a phase transfer catalyst which is selected from the group consisting of a Crown-ether and a compound having the formula $Q^+X^-$; wherein $Q^+$ is selected from the group consisting of a quaternary ammonium cation and a quaternary phosphonium cation; and wherein $X^-$ is an inorganic cation.

16. In a process for the carbamoylation of steroid or diphenylethane or diphenylethene phenolic hydroxy groups to form corresponding carbamate esters, comprising reacting in liquid phase the said compound and a tertiary carbamoyl chloride, the improvement which comprises using an aqueous alkali metal hydroxide and a phase transfer catalyst which is selected from the group consisting of a Crown-ether and a compound having the formula $Q^+X^-$, wherein $Q^+$ is selected from the group consisting of a quaternary ammonium cation and a quaternary phosphonium cation, wherein $X^-$ is an inorganic cation, and wherein the reaction is performed in one step using a catalytic amount of the phase transfer catalyst.

17. In a process for the carbamoylation of steroid or diphenylethane or diphenylethene phenolic hydroxy groups to form corresponding carbamate esters, comprising reacting in liquid phase the said compound and a tertiary carbamoyl chloride, the improvement which comprises using an aqueous alkali metal hydroxide and a phase transfer catalyst which is selected from the group consisting of a Crown-ether and a compound having the formula $Q^+X^-$, wherein $Q^+$ is selected from the group consisting of a quaternary ammonium cation and a quaternary phosphonium cation, wherein $X^-$ is an inorganic cation, and wherein the reaction is performed in two steps, the first step comprising reaction of the said phenolic compound, the aqueous alkali metal hydroxide, and phase transfer catalyst in at least an equivalent amount based upon the said phenolic compound, in a water-immiscible non-reactive organic solvent which is not reactive with the reactants or reaction products under the conditions of reaction and in which the ion-pair is soluble, followed by separation of the obtained organic phase containing the resulting ion-pair dissolved therein, and the second step comprising reaction of the ion-pair with the carbamoyl chloride to form the said desired carbamate ester.

18. Process of claim 16, wherein the phase transfer catalyst is used in an amount ranging from one to ten percent of the equivalent weight based upon the said phenolic compound.

19. Process of claim 16, wherein the reaction is performed in a water-immiscible non-reactive organic solvent.

20. Process of claim 17, wherein the organic phase, containing the ion-pair obtained in the first step, is used directly in the second step without isolation.

21. Process of claim 17, wherein the organic solvent is a chlorinated aliphatic hydrocarbon.

22. Process of claim 19, wherein the organic solvent is a chlorinated aliphatic hydrocarbon.

23. Process of claim 15, wherein the reaction is conducted at about room temperature.

24. Process of claim 15, wherein the cation is a quaternary ammonium cation.

25. Process of claim 15, wherein the carbamoyl chloride is a bis(omega-halo-lower alkyl)carbamoyl chloride.

26. Process of claim 15, wherein the phenolic compound is an estra-1,3,5(10)-triene, diphenyl-substituted ethane, or diphenyl-substituted ethene.

27. Process of claim 26, wherein the said phenolic compound is selected from the group consisting of: estrone, estradiol-17$\beta$, estradiol-17$\alpha$, estriol, 16-epiestriol, 17-epiestriol, 16$\alpha$-hydroxy-estrone, 16-ketoestradiol, 17$\alpha$-ethynylestradiol, diethylstilbestrol, dienestrol, and hexestrol; and esters and ethers of any of the foregoing.

28. Process of claim 24, wherein the organic groups in the quaternary ammonium cation are selected from alkyl and benzyl.

29. Process of claim 24, wherein the ion-pair consisting of the ion of estradiol-17$\beta$ and the quaternary ammonium cation is reacted with N-bis(2-chloroethyl)- carbamoyl chloride to form estradiol-3-N-bis(2-chloroethyl)carbamate.

30. Process of claim 29, wherein the cation is tetrabutyl ammonium or benzyl trimethyl ammonium.

31. Process of claim 15, wherein the cation is a quaternary phosphonium cation, the organic groups of which are selected from alkyl and benzyl.

32. Process of claim 15, wherein the inorganic anion is selected from the group consisting of $Cl^-$, $Br^-$, $HSO_4^-$, and $OH^-$.

* * * * *

UNITED STATES PATENT AND TRADEMARK OFFICE
CERTIFICATE OF CORRECTION

PATENT NO. : 4,081,461
DATED : March 28, 1978
INVENTOR(S) : Hans Jacob Fex, et al.

It is certified that error appears in the above-identified patent and that said Letters Patent are hereby corrected as shown below:

Col. 1, line 44; "hydroxy" should read --hydroxyl--
Col. 2, line 47; "in" should read --is--
Col. 4, line 16; "$Q^{30}$" should read --$Q^+$--
Col. 4, line 44; "Crown" should read --crown--
Col. 6, line 60; "parts" should read --pairs--
Col. 8, line 26; "Encyklopaedie" should read --Encyklopädie--
Col. 9, line 44; "19" should read --199--
Col. 9, line 50; the formulas run together. The beginning of the new formula should start with the word --diethylstilbestrol--
Col. 11, line 35; "9.3" should read --19.3--
Col. 11, line 56; "3tert" should read --3-tert--
Col. 12, line 27; "produt" should read --product--
Col. 12, line 33; "H), b 2.95" should read --H), 2.95--
Col. 12, line 37; "17β" should read --17α--
Col. 12, line 38; "17β" should read --17α--
Col. 12, line 43; "Solvent: ;i d$_6$" should read --Solvent: d$_6$--
Col. 12, line 64; "member" should read --number--
Col. 12, line 67; "H), b 7.0" should read --H), 7.0--
Col. 13, line 25; "chloride." should read --chloride,--
Col. 13, line 37; "crown-6." should read --crown-6,--

UNITED STATES PATENT AND TRADEMARK OFFICE
CERTIFICATE OF CORRECTION

PATENT NO. : 4,081,461
DATED : March 28, 1978
INVENTOR(S) : Hans Jacob Fex, et al.

It is certified that error appears in the above-identified patent and that said Letters Patent are hereby corrected as shown below:

Col. 13, line 67; "isoporpyl" should read --isopropyl--
Col. 14, line 43; "compound, and" should read --compound and--

*Signed and Sealed this*

*Twenty-second* Day of *August 1978*

[SEAL]

Attest:

RUTH C. MASON
*Attesting Officer*

DONALD W. BANNER
*Commissioner of Patents and Trademarks*